United States Patent
Carromeu

(10) Patent No.: US 11,193,159 B2
(45) Date of Patent: Dec. 7, 2021

(54) HIGH THROUGHPUT OPTICAL ASSAY OF HUMAN MIXED CELL POPULATION SPHEROIDS

(71) Applicant: StemoniX Inc., Eden Prairie, MN (US)

(72) Inventor: Cassiano Carromeu, San Diego, CA (US)

(73) Assignee: StemoniX Inc., Eden Prairie, MN (US)

( * ) Notice: Subject to any disclaimer, the term of this patent is extended or adjusted under 35 U.S.C. 154(b) by 218 days.

(21) Appl. No.: 16/035,039

(22) Filed: Jul. 13, 2018

(65) Prior Publication Data

US 2019/0017097 A1 Jan. 17, 2019

Related U.S. Application Data

(60) Provisional application No. 62/532,667, filed on Jul. 14, 2017.

(51) Int. Cl.

| | | |
|---|---|---|
| *C12Q 1/682* | (2018.01) | |
| *G01N 33/542* | (2006.01) | |
| *C12N 5/071* | (2010.01) | |
| *G01N 33/50* | (2006.01) | |
| *G01N 33/68* | (2006.01) | |
| *G01N 21/25* | (2006.01) | |
| *G01N 33/58* | (2006.01) | |

(52) U.S. Cl.
CPC ........... *C12Q 1/682* (2013.01); *C12N 5/0671* (2013.01); *G01N 33/5008* (2013.01); *G01N 33/5058* (2013.01); *G01N 33/6851* (2013.01); *G01N 21/253* (2013.01); *G01N 33/542* (2013.01); *G01N 33/582* (2013.01)

(58) Field of Classification Search
CPC .............. C12Q 1/682; G01N 33/6851; G01N 33/5008; G01N 33/5058; G01N 21/253; G01N 33/542; G01N 33/582; C12N 5/0671

See application file for complete search history.

(56) References Cited

U.S. PATENT DOCUMENTS

| | | | | |
|---|---|---|---|---|
| 6,214,563 B1 * | 4/2001 | Negulescu | ............... | C12Q 1/34 422/505 |
| 2004/0110123 A1 * | 6/2004 | Maher | .............. | G01N 33/48728 435/4 |

(Continued)

FOREIGN PATENT DOCUMENTS

| | | |
|---|---|---|
| EP | 2974751 | 1/2016 |
| WO | 2014141528 | 9/2014 |

(Continued)

OTHER PUBLICATIONS

Chattoraj, S; "Biological oscillations: Fluorescence monitoring by confocal microscopy," Jul. 5, 2016, Chemical Physics Letters, pp. 1-10, DOI: 10.1016/j.cplett.2016.07.007 (Year: 2016).*

(Continued)

*Primary Examiner* — Jennifer Wecker
*Assistant Examiner* — Michael Paul Shimek
(74) *Attorney, Agent, or Firm* — Schwegman Lundberg & Woessner, P.A.

(57) ABSTRACT

The present disclosure provides a method of performing a functional assay on human spheroids, e.g., three-dimensional human cell spheroids using, in one embodiment, a fluorometric imaging plate reader.

19 Claims, 6 Drawing Sheets

(56) References Cited

U.S. PATENT DOCUMENTS

| | | | |
|---|---|---|---|
| 2011/0143960 A1* | 6/2011 | LaBarbera | G01N 33/5011 506/10 |
| 2011/0212481 A1* | 9/2011 | Morgan | G01N 33/5005 435/29 |
| 2011/0274692 A1* | 11/2011 | White | G01N 33/557 424/139.1 |
| 2014/0051168 A1* | 2/2014 | Vukasinovic | C12N 5/0068 435/397 |
| 2016/0022870 A1* | 1/2016 | Noguchi | A61P 9/00 424/423 |
| 2017/0115275 A1 | 4/2017 | Rege et al. | |
| 2017/0369847 A1* | 12/2017 | Mei | C12N 5/0657 |

FOREIGN PATENT DOCUMENTS

| | | |
|---|---|---|
| WO | WO-2014141528 A1 | 9/2014 |
| WO | 2016115489 | 7/2016 |
| WO | WO-2016115489 | 7/2016 |

OTHER PUBLICATIONS

"International Application Serial No. PCT US2018 042105, Invitation to Pay Additional Fees and Partial Search Report dated Sep. 14, 2018", 10 pgs.

Edmondson,, Rasheena, "Three-Dimensional Cell Culture Systems and Their Applications in Drug Discovery and Cell-Based Biosensors", Assay and Drug Development Technologies 1 vol. 12 No. 4, (May 2014), 12 pgs.

Lee, Han Kyu, "Three Dimensional Human Neuro Spheroid Model of Alzheimers Disease Based on Differentiated Induced Pluripotent Stem Cells", PLOS ONE DOI:10.1371 journal.pone 0163072, (Sep. 29, 2016), 23 pgs.

Sirenko, Oksana, "Phenotypic Characterization of Compound Effects on iPSC-derived Cardiac and Liver Spheroids Using Fast Kinetic Fluorescence and 3D Image Analysis", Molecular Devices LLC, Cellular Dynamics Int, [Online] Retrieved from the Internet: https: www.moleculardevices.com sites default files en asset dd case-study phenotypic-characterization-of-compound.pdf, 1 pg.

Sirenko, Oksana, "Phenotypic Characterization of Toxic Compound Effects on Liver Spheroids Derived from iPSC Using Confocal Imaging and Three-Dimensional Image Analysis", Assay and Drug Development Technologies vol. 14 No. 7, (Sep. 2016), 382-395.

Sloan, "Human Astrocyte Maturation Captured in 3D Cerebral Cortical Spheroids Derived from Pluripotent Stem Cells.", Neuron, 95:779 (2017), Abstract only per attorney, (Aug. 2017), 2 pages.

Stephanie, M Ravenscroft, "Cardiac Non-myocyte Cells Show Enhanced Pharmacological Function Suggestive of Contractile Maturity in Stem Cell Derived Cardiomyocyte Microtissues", Toxicological Sciences vol. 152 No. 1, (Apr. 28, 2016), 99-112.

"International Application Serial No. PCT US2018 042105, International Search Report dated Oct. 30, 2018", 7 pgs.

"International Application Serial No. PCT US2018 042105, Written Opinion dated Oct. 30, 2018", 9 pgs.

"International Application Serial No. PCT US2018 042105, International Preliminary Report on Patentability dated Jan. 23, 2020", 11 pages.

"European Application Serial No. 18753497.9, Response filed Sep. 9, 2020 to Communication Pursuant to Rules 161(1) and 162 EPC dated Apr. 22, 2020", 10 pgs.

"Japanese Application Serial No. 2020-501302, Notification of Reasons for Refusal dated Mar. 2, 2021", with English translation, 7 pages.

Ravenscroft et al., Toxicology Sci. 152:99 (2016).

Terrasso et al., J. Biotechnol. 205:82 (2015).

Oksana, Sirenko, "Phenotypic Assays for Characterizing Compound Effects on Induced Pluripotent Stem Cell-Derived Cardiac Spheroid", Assay and Drug Development Technologies vol. 15 No. 6, (Aug. 1, 2017), 280-296.

Terrasso, Ana Paula, "Novel scalable 3D cell based model forin vitroneurotoxicity testing: Combining human differentiated neurospheres with gene expression and functional endpoints", Journal of Biotechnology, Elsevier, Amsterdam, NL, vol. 205, (Jan. 5, 2015), 11 pgs.

"Japanese Application Serial No. 2020-501302, Response filed Jun. 2, 2021 to Notification of Reasons for Refusal dated Mar. 2, 2021", w/ English claims, 23 pgs.

U.S. Appl. No. 17/238,315, filed Apr. 23, 2021, High throughput Optical assay of Human Mixed Cell Population Spheroids.

Sirenko, Oksana, "Phenotypic Assays for Characterizing Compound Effects on Induced Pluripotent Stem Cell-Derived Cardiac Spheroids", Assay and Drug Development Technologies vol. 15, No. 6, (Aug. Sep. 2017), 17 pages.

\* cited by examiner

Plate 10 with 384 wells, each having a spheroid 20

384w microBrain 3D plate

Spheroid 20

Graph showing 8 peaks 30.

| Compound | Mechanism of Action |
|---|---|
| CNQX | Potent AMPA/kainate receptor antagonist. Also antagonist at glycine modulatory site on NMDA receptor complex |
| NBQX | Potent, selective and competitive AMPA receptor antagonist |
| MK-801 | A potent, selective and non-competitive NMDA receptor antagonist |
| Muscimol | Potent $GABA_A$ receptor agonist |

HIGH THROUGHPUT OPTICAL ASSAY OF HUMAN MIXED CELL POPULATION SPHEROIDS

CROSS-REFERENCE TO RELATED APPLICATIONS

This application claims the benefit of the filing date of U.S. application Ser. No. 62/532,667, filed on Jul. 14, 2017, the disclosure of which is incorporated by reference herein.

BACKGROUND

The accelerating pace of drug discovery has spawned an increasing need for functional in vitro assays using living human cells. Automating these assays for high-throughput systems, however, has proven to be difficult. Noting that the most common biological assays employed in high-throughput settings rely on some kind of fluorescent measurement.

Fluorometric Imaging Plate Reader, otherwise known as the FLIPR, is a unique combination of optics, automated pipetting, and temperature control. Designed to perform high-throughput screening assays using adherent and non-adherent cells, FLIPR is ideally suited for kinetic, cell-based assays such as measuring changes in intracellular calcium levels and membrane potential.

FLIPR integrates a powerful argon laser, a CCD (charged couple device) imaging camera, an optical detection scheme, and a programmable 96-well pipettor to perform fluorometric analyses on all 96 wells of a microplate simultaneously. The system generates real-time kinetic data by stimulating and reading all 96 wells in 1-second intervals. Typically, the argon laser excites a suitable fluorescent dye. The resultant emitted light is detected by a cooled CCD camera that acts as an integrated detector, accumulating signal over the duration of the exposure. Sensitivity is further enhanced by the FLIPR's optical scheme, which limits the depth of field of the CCD camera to a few hundred microns on the bottom of each well, or essentially at the level of the cell monolayer. This technique reduces the background fluorescence from extracellular dye by about an order of magnitude. Taken together, these systems combine into an extremely sensitive fluorescence detector.

The FLIPR instruments capture real-time kinetic data, enabling the identification of a potential drug hit within seconds of its addition to an assay. Indeed, one of the features of FLIPR technology is its data fidelity, allowing researchers to monitor single-well determinations. The software also performs data analysis and reduction and can export data to spreadsheet programs.

The use of FLIPR with 2 dimensional cell formats in which the cells of interest are added to a microplate well and form a monolayer across the well bottom has proven to be problematic because the cells do not always fill the wells uniformly or attached with high fidelity. This leads to inconsistent data generation measured by FLIPR within a plate and also from plate to plate. When conducting a high throughout screen on 96, 384 or 1536 well plates, data consistency is needed to generate meaningful information on drug interaction or drug kinetic data.

SUMMARY

Surprisingly, the modulation of calcium oscillations by drug molecules on a 3D spheroid can be monitored and the resulting data is quite consistent, e.g., spheroid neuron synapses fired predictably and consistently for long periods of time. In one embodiment, the disclosure provides an optical assay, e.g., a functional FLIPR assay or high content high magnification optical microscopy, of 3D human cell spheroids, e.g., mixed population human cell neuron spheroids. In one embodiment, prior to testing, spheroids are cultured for 4 to 16 weeks to induce robust synchronized synaptic networks to mimic mature human like brain functionality. Those mixed population spheroids fired predictably and consistently for long periods of time. In one embodiment, the disclosure provides a high throughput optical assay of a mixed population of human cell 3D spheroids utilizing FLIPR and calcium uptake fluorescence oscillations. The oscillations may be modulated with chemical compounds, and oscillatory firing can be altered with agonist or antagonists.

In one embodiment, the disclosure provides an optical method to detect the effect of one or more compounds on spheroids. The method includes contacting a tissue culture plate, e.g., one having wells, comprising one or more spheroids of human cells including those of uniform diameter and one or more test compounds; and optically detecting the amount or change in oscillations in the spheroids. In one embodiment, the plate is a multi-well plate. In one embodiment, the spheroids are further contacted with a fluorescent molecule useful to detect calcium, and the amount or change in fluorescence over time is detected. In one embodiment, the amount or change in fluorescence detects a quantity of peaks of fluorescence, an amplitude of one or more of the peaks, peak spacing between one or more of the peaks, a width of one or more peaks, or any combination thereof. In one embodiment, the spheroids comprise neurons. In one embodiment, the spheroids comprise neurons and astrocytes. In one embodiment, the spheroids comprise heart, liver, kidney, pancreas, lung, endothelial or epithelial cells. In one embodiment, the spheroids comprise cancer cells or immortalized cells. In one embodiment, the spheroids comprise microglial cells or oligodendrocytes. In one embodiment, the spheroids comprise pericytes and endothelial cells. In one embodiment, the spheroids comprise endothelial cells, microglial cells, neurons, oligodendrocytic cells, or any combination thereof. In one embodiment, the cells are differentiated cells. In one embodiment, wherein the cells are progenitor cells such as human iPSCs. In one embodiment, the progenitor cells are progenitors of neurons, astrocytes, heart cells, liver cells, kidney cells, pancreas cells, lung cells, endothelial cells, or epithelial cells. In one embodiment, the spheroids have a diameter of about 500 to about 600 microns. In one embodiment, the spheroids have a diameter of about 450 to about 500 microns. In one embodiment, the spheroids are cultured for at least 4 to 6 weeks before contacting with the one or more test compounds. In one embodiment, the fluorescent molecule comprises Calcium 3, Calcium 4, Calcium 5, Calcium 6, Fluo 3, or Fluo 4, or a combination thereof. In one embodiment, the spheroids are further contacted with a cell membrane impermeant quencher. In one embodiment, the amount of change in fluorescence is compared to the fluorescence with spheroids and the fluorescent molecule but no test compound. In one embodiment, in a multi-well plate, each well has one spheroid.

Also provided is a multi-well plate comprising one or more mixed human cell spheroids per well. In one embodiment, the spheroids comprise neurons and astrocytes. In one embodiment, the spheroids comprise heart, liver, kidney, pancreas, lung, endothelial or epithelial cells. In one embodiment, the spheroids comprise microglial cells or oligodendrocytes. In one embodiment, the spheroids comprise pericytes and endothelial cells. In one embodiment, the spheroids comprise endothelial cells, microglial cells, neurons, oligodendrocytic cells, or any combination thereof. In one embodiment, the spheroids comprise progenitors of neurons, astrocytes, heart cells, liver cells, kidney cells, pancreas cells, lung cells, endothelial cells, or epithelial cells. Different wells may have different spheroid types.

These and other objects and advantages of the invention will become apparent from reading and understanding the following detailed description.

DETAILED DESCRIPTION

The following discussion is directed towards various embodiments of the invention. Although one or more of these embodiments may be preferred, the invention is not limited to the embodiments disclosed. In addition, one skilled in the art will understand that the following description has broad application, and the discussion of any embodiment is meant only to be exemplary of that embodiment, and not intended to limit the scope of the disclosure or claims to that embodiment.

Figure 1:
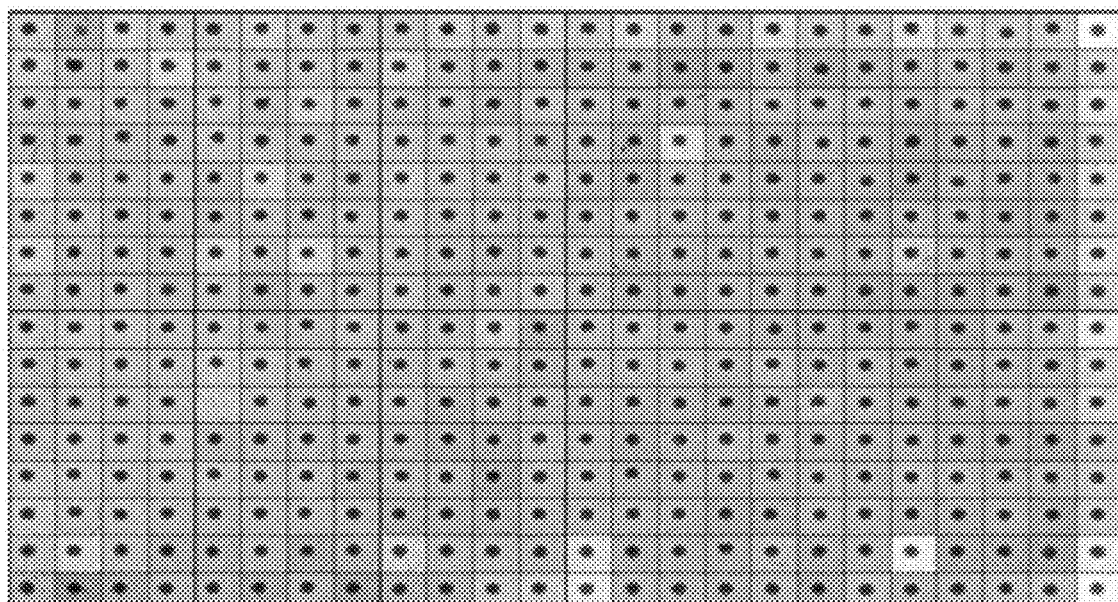
FIG. 1 is an image of an exemplary 384 well microplate with 1 mixed cell spheroid located in each well, to demonstrate one embodiment of the present subject matter.

FIG. 1 is an image of an exemplary 384 well microplate with 1 mixed cell spheroid located in each well, to demonstrate one embodiment of the present subject matter. In this example, 24 columns of 16 cells of the microplate provide the 384 wells. FIG. 1 shows an actual black and white image of an entire 384 well microplate 10 into which each well is formed a spheroid 20 having a mixed population of astrocytes and neurons that forms a structure that is approximately 500 microns in diameter. The microplate can have, in one embodiment, 96, 384 or 1536 wells. Other numbers of wells are possible without departing from the scope of the present subject matter. The spheroids 20 may be formed by adding individual cells into each well that subsequently spontaneously form into different size spheroids depending on the number of cells that are initially added. The number of cells inserted into each well can range from hundreds to hundreds of thousands depending on well size and the diameter of the spheroid desired for the assay. In one embodiment, approximately 20,000 human cells, e.g., iPS cells, are added to the well and form a spheroid of approximately 500 microns in diameter.

In FIG. 1, a microBrain™ 3D plate is used to demonstrate the microplate; however, it is understood that other microplates and structures may be used to create a plurality of wells.

Figure 2:
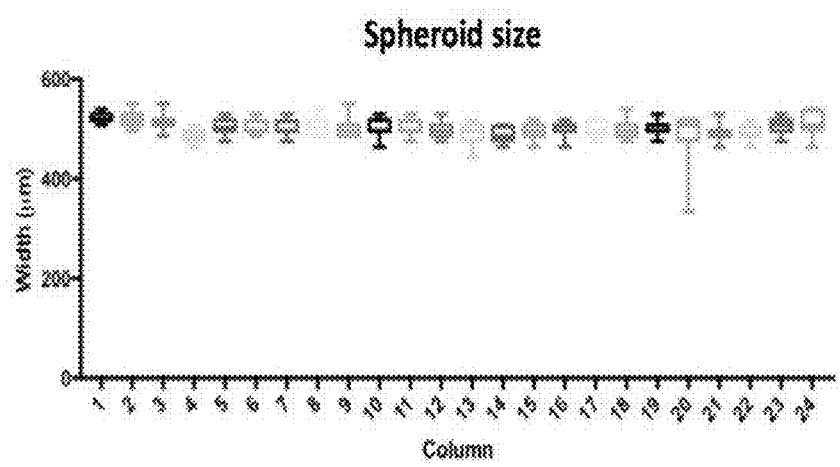
FIG. 2 is a plot of average mixed cell spheroid size across a number of columns in a 384 well microplate in one example of an application of the present subject matter.

FIG. 2 shows a plot of spheroid 20 diameters (i.e., "width") vs. location across the 24 columns of a 384 well microwell plate. As can be seen from the data the diameter uniformity and size is very consistent. The ratio of the astrocyte to neurons in the mixed population can range from about 5 to about 95 percent, about 10 to about 90 percent, about 20 to about 80 percent, about 40 to about 60 percent, about 60 to about 40 percent, about 80 to about 20 percent, about 90 to about 10 percent, or about 95 to about 5 percent, e.g., a ratio of 50/50 may mimic what is found in the human brain. The cells used to form the spheroids can be derived from human primary cell lines, human iPScs or human engineered immortal cell lines. Also the spheroids are not limited to only neurons but can also be heart, liver, kidney, pancreas, lung, endothelial and epithelial cells as well as solid tumor cell lines. Other cells may be used without departing from the scope of the present subject matter.

Figure 3:
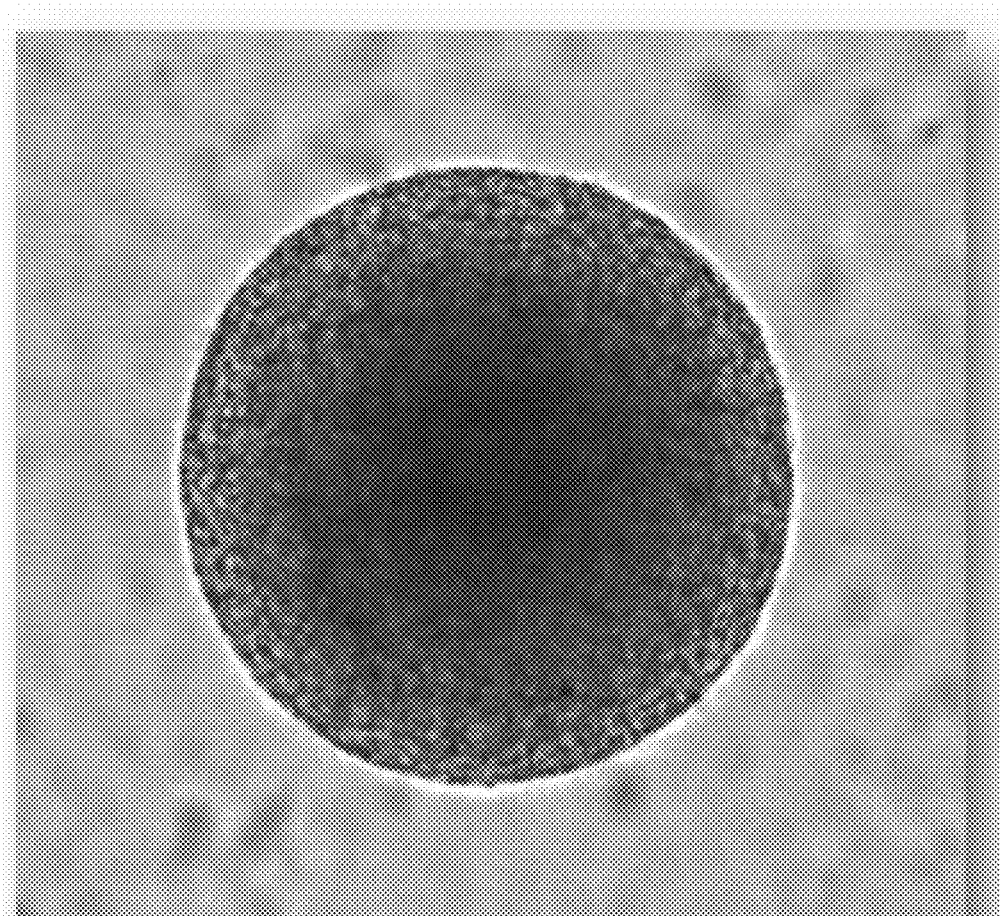
FIG. 3 is an image of a mixed population neuron spheroid.

FIG. 3 shows a black and white image of an actual mixed population neuron spheroid 20 from an individual well within a microwell plate. What is unique about neuron spheroids is that they self organize into very uniform round geometries. The diameter of the spheroids can range from about 100 microns to about 10 millimeters, e.g., about 200 to 600 microns in diameter, e.g., about 300 to about 500 microns in diameter, about 400 to about 600 microns in diameter, or about 450 to about 650 microns in diameter, or about 475 to about 525 in diameter, e.g., an average of about 500 microns in diameter. In this particular example the ratio of astrocytes to neurons is approximately 50/50.

Figure 4:
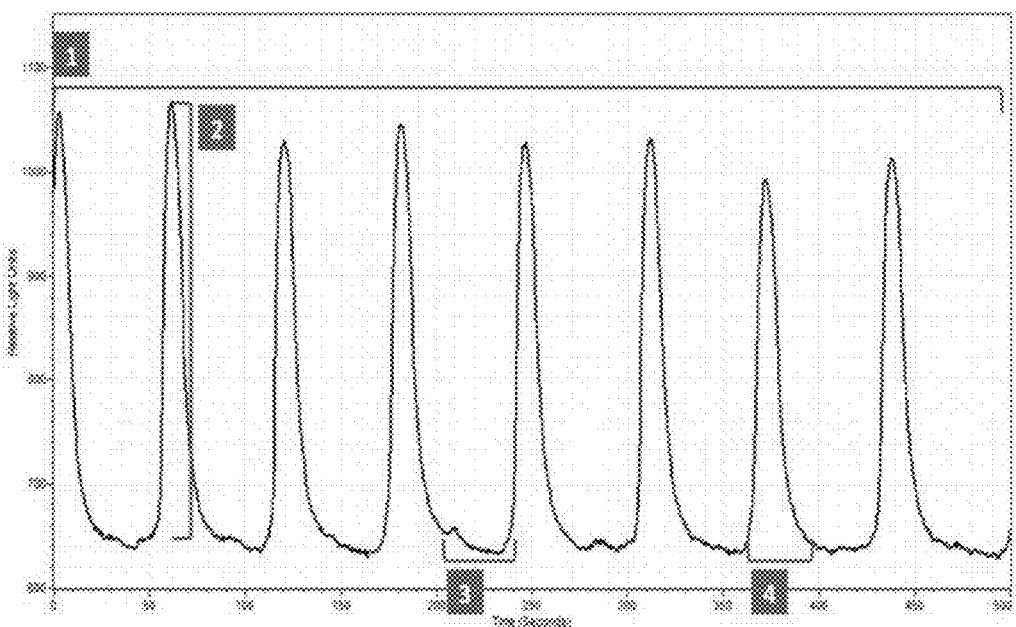
FIG. 4 is a FLIPR control plot of fluorescence generated by a spheroid from a micro plate well.

Referring to FIG. 4, this plot show the type of data generated by a FLIPR assay on a mixed population neuron spheroid 20 as a function of time. The parameters that are measured are peak count 1, peak amplitude 2, peak spacing 3, and peak width 4. All of these variables may be employed when interpreting the data generated by a FLIPR assay. They are indirect measurements of how the cells are behaving at steady state (no drug challenge) and how drugs are interacting with the cells in the spheroid 20. The peaks 30 represent spontaneous fluorescing calcium oscillations being generated by the spheroid in culture media. Data for each cell can be obtained and stored using FLIPR.

Figure 5:
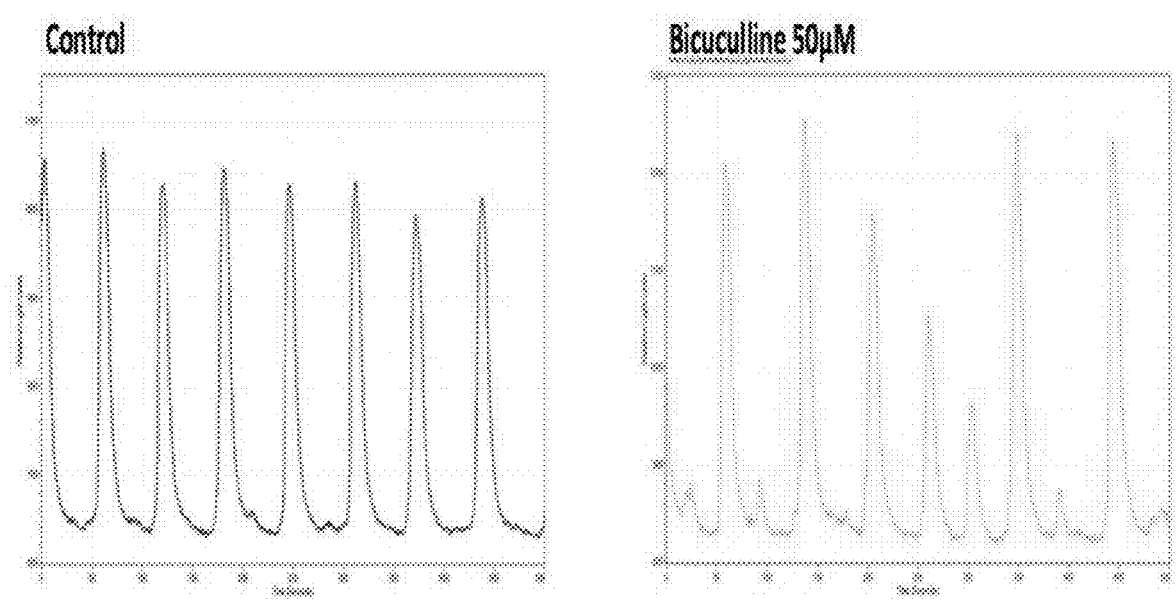
FIG. 5 is a FLIPR data plot of a spheroid control well vs. drug challenged well, demonstrating variation of response for a drug challenged well versus a control well, to demonstrate one application of the present subject matter.

FIG. 5 shows the effect of the drug Biculline that is a GABAergic antagonist at a 50 micro molar concentration on inducing an irregular and erratic calcium uptake behavior in the spheroids 20 vs. the controls. The axes of the figure show "Relative Light Units" and "Time (Seconds)." A comparison of the Biculline drug peaks to those of the control shows almost all of the measurement parameters are altered such as peak number, spacing and height. The same type of response was also observed using Glutametergic antagonist as well but at higher dose concentrations. It should be noted that the age of the spheroids may have an effect on the drug interactions. In the one embodiment, the spheroids can range in age from 2 to over 52 weeks old in order to simulate more mature cells as found in in vivo models. In one embodiment, 5 to 10 week old spheroids 20 are employed. For example, aged spheroids formed of neurons, e.g., aged about 8 weeks, allow for more synapse connections.

Figure 6:
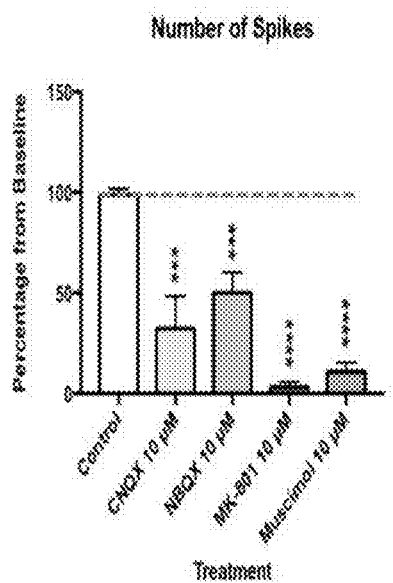
FIG. 6 is a summary of various Glutametergic and Gabaergic antagonists and agonist effects on spheroids as measured by FLIPR, in one example application of the present subject matter.

FIG. 6 is a summary of some of the results obtained using the FLIPR assay and spheroids. The graph on the left shows the change in the number of calcium oscillation peaks generated before (control) and after exposure to well known Glutametergic and Gabaergic agonists and antagonists small molecule drug compounds used from the table on the right. As can be seen from the graph on the right there is a significant and immediate modulation of the spheroid 20 calcium oscillations with the exposure to the listed drug compounds. This type of chemically induced response can be the basis for an epilepsy seizure model that mimics what is observed in humans. Therefore, this 3D spheroid model for example can be used as a high throughput-screening tool for drugs that can rescue erratic neuron synapse firing that is the basis for seizures and other diseases.

Thus, in one embodiment, the present disclosure provides a method of performing a functional assay on a mixed population of three-dimensional human cell spheroids using, in one embodiment, a fluorometric imaging plate reader. For example, very uniform and consistent mixed population spheroids, e.g., astrocyte and neuron spheroids, may be generated from differentiated human iPS cells. The spheroids may range in diameter from, in one embodiment, about 500 to about 600 microns, and may be formed in wells of a multi-well plate, e.g., formed in a 384 well micro plate. The spheroids are then contacted with one or more molecules, e.g., Gabaergic and Glutametergic modulating small molecules. The temporal response of calcium oscillation fluorescent light intensity of the spheroids may be captured and quantified in real time and is a measure of the cell spheroid response to drug challenges and concentration gradients.

Some Examples of the Present Subject Matter

Spheroids, such as those formed from two or more different cell types, may be prepared using any suitable medium, optionally including one or more different growth factors, and any suitable conditions. For example, spheroids formed from neurons and astrocytes may be prepared using, in one embodiment, one or more of the following media and/or conditions: BrainPhys™ Neuronal Medium (StemCell Tech) supplemented 1× with SM1 Neuronal Supplement (BrainPhys™ Neuronal Medium and SM1 Kit (cat. #05792; StemCell Technologies), 20 ng/mL BDNF (cat. #78005; StemCell Technologies), 20 ng/mL GDNF (cat. #78058; StemCell Technologies) and penicillin/streptomycin (cat. # SV30010; GE Healthcare Life Sciences). The cells are maintained at 37° C. in an incubator with 5% $CO_2$ and high humidity.

The present subject matter allows for multiple approaches for analyzing the effects of one or more compounds on spheroids, comprising contacting a multi-well plate having wells comprising spheroids of human cells of uniform diameter, a fluorescent molecule useful to detect calcium, and one or more test compounds; and optically detecting the amount or change in fluorescence over time in each well. In various examples, the method detects the amount or change in fluorescence via a quantity of peaks of fluorescence, an amplitude of one or more of the peaks, peak spacing between one or more of the peaks, a width of one or more peaks, or any combination thereof. In various examples, the foregoing methods may include wherein the spheroids comprise neurons or wherein the spheroids comprise neurons and astrocytes, or wherein the spheroids comprise heart, liver, kidney, pancreas, lung, endothelial or epithelial cells, or wherein the spheroids comprise cancer cells. In various of the preceding examples, the spheroids may comprise a plurality of different cell types. In the foregoing examples, some examples include wherein the cells are derived from human iPSCs. In some examples, the cells are differentiated cells. In some examples, the cells are progenitor cells. In some examples using progenitor cells, the progenitor cells are progenitors of neurons, astrocytes, heart cells, liver cells, kidney cells, pancreas cells, lung cells, endothelial cells, or epithelial cells. In some of the foregoing examples, the cells are immortalized cells.

In various of the foregoing methods, the spheroids may have a diameter of about 500 to about 600 microns or a diameter of about 450 to about 500 microns. In various of the foregoing methods, the spheroids may have been in culture for at least 6 weeks. In various of the foregoing methods, including a fluorescent molecule, the molecule comprises Calcium 3, Calcium 4, Calcium 5, Calcium 6, Fluo 3, or Fluo 4.

In one embodiment, an optical assay is provided, e.g., a functional FLIPR assay or high content high magnification optical microscopy, of 3D human cell spheroids, e.g., spheroids formed of mixed populations of neurons, oligodendrocytes, microglial cells, endothelial cells, or any combination thereof.

In one embodiment, a multi-well optical assay is provided, such as a functional FLIPR assay, of 3D mixed population human cell spheroids in a multi-well format, e.g., a 96, 384 or 1536 microplate well, e.g., spheroids in a rounded bottom well format.

Further provided is an optical assay, e.g., a functional FLIPR assay, of 3D mixed population spheroids in which the spheroids in each microplate well are of uniform size, e.g., diameters that are +/−50 or +/−25 microns. In one embodiment, FLIPR generates real time functional data on 3D neuron based cell spheroids that are very consistent within a micro plate, e.g., well-to-well, and from plate to plate.

In one embodiment, the disclosure provides an optical assay including a functional FLIPR assay of 3D mixed population spheroids that respond to agonist or antagonist drug challenge in real time.

In one embodiment, the disclosure provides an optical assay, e.g., a functional FLIPR assay, of 3D mixed population spheroids derived from human primary cells, iPSc, differentiated cells, or various immortal human cell lines.

In various of the foregoing methods, further comprising contacting the wells with a cell membrane impermeant quencher. In any of the foregoing methods the amount of change in fluorescence can be compared to the fluorescence in a well with spheroids and the fluorescent molecule but no test compound.

Those skilled in the art will understand other examples and variations are possible without departing from the scope of the present subject matter.

The above discussion is meant to be illustrative of the principle and various embodiments of the present invention. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention Thus, numerous variations and modifications will become apparent to those skilled in the art once the above disclosure is fully appreciated. For example the invention is not limited to neurons or mixed populations of neurons. The invention can be applied to all organ types found in humans such as heart, lung, liver, kidney, colon, pancreas and cancer mixed population cell spheroids to name a few. It is intended that the following claims be interpreted to embrace all such variations and modifications.

What is claimed is:

1. An optical method to detect the effect of one or more compounds on spheroids, comprising: contacting one or more spheroids comprising human cells of uniform diameter and one or more test compounds; and optically detecting the amount or change in spontaneous oscillations of one or more of the spheroids, wherein the amount or change in the spontaneous oscillations of the one or more of the spheroids is detected with a fluorescent molecule.

2. The method of claim 1 wherein the one or more spheroids are in wells of a multi-well plate.

3. The method of claim 2 wherein each well has one spheroid.

4. The method of claim 2 wherein the wells are further contacted with a fluorescent molecule useful to detect calcium, and the amount or change in fluorescence over time is detected in one or more wells.

5. The method of claim 4 wherein the amount or change in fluorescence detects a quantity of peaks of fluorescence, an amplitude of one or more of the peaks, peak spacing between one or more of the peaks, a width of one or more peaks, or any combination thereof.

6. The method of claim 1 wherein the one or more spheroids comprise neurons.

7. The method of claim 1 wherein the one or more spheroids comprise neurons and astrocytes.

8. The method of claim 1 wherein the one or more spheroids comprise heart, liver, kidney, pancreas, lung, endothelial or epithelial cells.

9. The method of claim 1 wherein the one or more spheroids comprise cancer cells or immortalized cells.

10. The method of claim 1 wherein the one or more spheroids comprise microglial cells or oligodendrocytes.

11. The method of claim 1 wherein the one or more spheroids comprise pericytes and endothelial cells.

12. The method of claim 1 wherein the one or more spheroids comprise endothelial cells, microglial cells, neurons, oligodendrocytic cells, or any combination thereof.

13. The method of claim 1 wherein the cells are progenitor cells.

14. The method of claim 1 wherein the one or more spheroids have a diameter of about 500 to about 600 microns.

15. The method of claim 1 wherein the one or more spheroids have a diameter of about 450 to about 500 microns.

16. The method of claim 1 wherein the one or more spheroids are cultured for at least 4 to 6 weeks before contacting with the one or more test compounds.

17. The method of claim 1 which further comprises contacting the one or more spheroids with a cell membrane impermeant quencher.

18. The method of claim 1 wherein the amount of change in fluorescence is compared to the fluorescence with spheroids and the fluorescent molecule but no test compound.

19. A method to detect the effect of one or more compounds on spheroids, comprising: contacting one or more spheroids having a diameter of about 500 to about 600 microns which spheroids comprise human neurons and astrocytes, one or more test compounds and a fluorescent molecule; and detecting the amount or change in fluorescent oscillations of one or more of the spheroids.

* * * * *